US010215763B2

(12) United States Patent
Soto et al.

(10) Patent No.: US 10,215,763 B2
(45) Date of Patent: Feb. 26, 2019

(54) METHODS FOR ESTIMATING PRION CONCENTRATION IN FLUIDS AND TISSUE BY QUANTITATIVE PMCA

(75) Inventors: Claudio Soto, Friendswood, TX (US); Baian Chen, Beijing (CN); Rodrigo Morales, Houston, TX (US)

(73) Assignee: BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 658 days.

(21) Appl. No.: 13/110,899

(22) Filed: May 18, 2011

(65) Prior Publication Data

US 2011/0311997 A1 Dec. 22, 2011

Related U.S. Application Data

(60) Provisional application No. 61/345,760, filed on May 18, 2010, provisional application No. 61/345,940, filed on May 18, 2010.

(51) Int. Cl.
*G01N 33/68* (2006.01)
*G01N 1/28* (2006.01)

(52) U.S. Cl.
CPC . *G01N 33/6896* (2013.01); *G01N 2001/2893* (2013.01); *G01N 2800/2828* (2013.01)

(58) Field of Classification Search
CPC combination set(s) only.
See application file for complete search history.

(56) References Cited

U.S. PATENT DOCUMENTS 7,351,526 B2 * 4/2008 Soto et al. ........................ 435/5

OTHER PUBLICATIONS

Soto et al., TINS, vol. 25, 2002, pp. 390-394.*
Saborio et al., Nature, vol. 411, 2001, pp. 810-813.*
Saá et al; J Biol Chemistry 281(46): 35245-35252, Nov. 17, 2006, plus supplemental figure.*
Chen et al., Nature Methods, vol. 7 No. 7, Epub May 30. (Year: 2010).*
D'Castro, et al., "Isolation of Proteinase K-Sensitive Prions Using Pronase E and Phosphotungstic Acid" PLoS One, 2010, 5(12), e15679.
Onisko, et al., "Probing PrPSc Structure Using Chemical Cross-Linking and Mass Spectrometry: Evidence of the Proximity of Gly90 Amino Termini in the PrP 27-30 Aggregate." Biochemistry, 2005, 44, 10100-10109.
Atarashi, et al., "Real-time quaking-induced conversion—A highly sensitive assay for prion detection." Prion 2011, 5(3), 150-153.
Deleault, et al., "Formation of native prions from minimal components in vitro." Proc. Nat. Acad. Sci. 2007, 104, 9741-9746.

* cited by examiner

*Primary Examiner* — Kimberly Ballard
*Assistant Examiner* — Stacey N MacFarlane
(74) *Attorney, Agent, or Firm* — Benesch Friedlander Coplan & Aronoff LLP; Kraig K. Anderson; Benjamen E. Kern

(57) ABSTRACT

The present embodiments disclose methods for estimating $PrP^{Sc}$ concentration in fluids and tissues by quantitative PMCA.

10 Claims, 8 Drawing Sheets

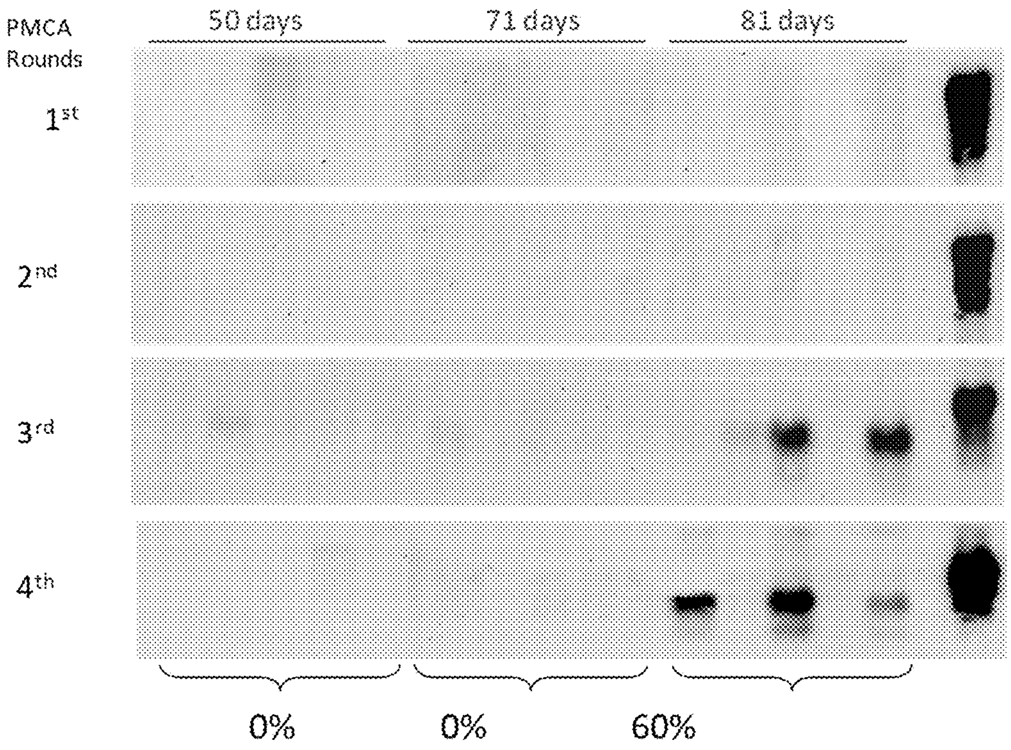
Figure 6, cont.

METHODS FOR ESTIMATING PRION CONCENTRATION IN FLUIDS AND TISSUE BY QUANTITATIVE PMCA

CROSS-REFERENCE TO RELATED APPLICATIONS

This application claims priority from U.S. Provisional Patent Application No. 61/345,940, filed May 18, 2010, and U.S. Provisional Patent Application No. 61/345,760, filed May 18, 2010, both of which are incorporated by reference herein in their entireties.

STATEMENT REGARDING FEDERALLY SPONSORED RESEARCH OR DEVELOPMENT

This invention was made with Government support under R01NS049173 and P01AI077774 awarded by the National Institutes of Health. The Government has certain rights in the invention.

BACKGROUND

Transmissible spongiform encephalopathies (TSE), also known as prion diseases, are a group of neurodegenerative diseases that affect humans and animals. Creutzfeldt-Jakob disease (CJD), kuru, Gerstmann-Straussler-Scheiker diseases (GSS), and fatal familial insomnia (FFI) in humans, as well as scrapie and bovine spongiform encephalopathy (BSE) in animals, are examples of TSE diseases.

It is known that a key characteristic and marker of prion diseases is the formation of an abnormally shaped protein named $PrP^{Sc}$. However, prion diseases are characterized by an extremely long incubation period. Thus, concentrations of $PrP^{Sc}$ are at low levels for a long period of time. As such, one important objective of prion research has been to detect small amounts of $PrP^{Sc}$ in diverse samples.

$PrP^{Sc}$ is a post-translationally modified version of a normal protein, termed $PrP^C$. $PrP^C$ is found naturally on the membranes of animal and human cells. The infective unit of $PrP^{Sc}$ is understood to be a β-sheet rich oligomeric structure, which converts $PrP^C$ to $PrP^{Sc}$ by integrating $PrP^C$ into a growing aggregate (FIG. 1). In light of this replication model, it has been found that $PrP^{Sc}$ can be detected with high sensitivity by protein misfolding cyclic amplification (PMCA). See U.S. Pat. No. 7,351,526 and U.S. Patent Application Pub. No. 2006/0263767, each of which is incorporated by reference herein it its entirety. In the context of prion diseases, PMCA-based $PrP^{Sc}$ detection typically involves: (i) contacting a sample with $PrP^C$ (e.g., by contacting a suspected diseased sample with a tissue homogenate containing $PrP^C$); (ia) incubating the sample/$PrP^C$ mixture; (ii) disaggregating any aggregates formed during step (ia) (e.g., by sonication); (iii) repeating steps (ia) and (ii) a plurality of times; and (iv) detecting the presence of $PrP^{Sc}$ within the sample (e.g., by western blotting). See FIG. 2.

What is still needed in the art, however, is a quantitative procedure for determining the concentration—rather than merely detecting the presence—of $PrP^{Sc}$ in fluids and tissues. The present embodiments disclose such a procedure.

SUMMARY

In one embodiment, a method for estimating the concentration of $PrP^{Sc}$ in a sample is provided.

In one aspect of the method, a calibration curve is provided, by:

preparing a plurality of stock solutions, each having a known concentration of $PrP^{Sc}$;

separately mixing each of the stock solutions with a first $PrP^C$ source to form separate stock reaction mixes;

performing a plurality of protein misfolding cyclic amplification cycles on the separate stock reaction mixes, each cycle comprising:

incubating the stock reaction mix; and disrupting the stock reaction mix;

subjecting the separate amplified stock reaction mixes to an assay after each cycle, until a prion signal is detected;

comparing the concentration of each stock solution with the number of cycles required to detect the prion signal; and plotting the comparison in the form of a standard calibration curve.

In another aspect of the method, the calibration curve is used to estimate the concentration of $PrP^{Sc}$ in the sample, by:

mixing the sample with a second $PrP^C$ source to form a sample reaction mix;

performing a plurality of protein misfolding cyclic amplification cycles on the sample reaction mix, each cycle comprising:

incubating the sample reaction mix; and disrupting the sample reaction mix;

subjecting the amplified sample reaction mix to an assay after each cycle, until a $PrP^{Sc}$ signal is detected; and comparing the number of cycles required to detect the $PrP^{Sc}$ signal to the calibration curve.

In another embodiment, a method for estimating the concentration of prion in a sample is provided, the method comprising:

mixing the sample with a non-pathogenic protein to form a reaction mix;

performing a plurality of protein misfolding cyclic amplification cycles on the reaction mix, each cycle comprising:

incubating the reaction mix; and disrupting the reaction mix;

subjecting the amplified reaction mix to an assay after each cycle, until a prion signal is detected; and comparing the number of cycles required to detect the prion signal to a predetermined calibration curve.

In another embodiment, a kit for detecting and quantifying prion in a sample is provided, the kit comprising:

(a) a non-pathogenic protein;

(b) a sonicator; and (c) a calibration curve.

BRIEF DESCRIPTION OF THE DRAWINGS

The accompanying figures, which are incorporated in and constitute a part of the specification, illustrate various methods, results, and so on, and are used merely to illustrate various example embodiments.

DETAILED DESCRIPTION

The present embodiments disclose a method for estimating $PrP^{Sc}$ concentration in fluids and tissues by quantitative PMCA.

In one embodiment, a calibration curve is determined. For example, a plurality of stock solutions is prepared, each having a known concentration of $PrP^{Sc}$. The stock solutions are separately mixed with a first $PrP^{C}$ source to form separate stock reaction mixes. The stock reaction mixes are incubated and subjected to sonication. The incubation and sonication steps may be repeated a plurality of times, until a $PrP^{Sc}$ signal is detected (by, e.g., western blotting) for each stock reaction mix. The concentration of each stock solution is compared with the number of times the incubation and sonication steps were repeated, to determine a calibration curve.

In one particular embodiment, $PrP^{Sc}$ was partially purified by precipitation in the presence of sarkosyl. This partially purified $PrP^{Sc}$ was used as a stock solution in buffer. To estimate the $PrP^{Sc}$ concentration in the stock solution, partially purified $PrP^{Sc}$ in the stock solution was subjected to deglycosylation and, subsequently, to western blot assay. To determine the $PrP^{Sc}$ concentration of the stock solution, the stock solution western blot assay signal was compared to western blot and enzyme-linked immunosorbent assay signals of known concentrations of $PrP^{Sc}$.

Once the $PrP^{Sc}$ concentration of the stock solution was estimated, the stock solution was diluted and separated into several sub-solutions having various known $PrP^{Sc}$ concentrations ranging from $1\times10^{-8}$ to $1\times10^{-19}$ g. The sub-solutions were separately spiked into separate normal hamster brain homogenates to form stock reaction mixes. The stock reaction mixes were subjected to serial rounds of PMCA cycles. In one particular embodiment, one "round" of PMCA cycles corresponded to 144 cycles. More or fewer than 144 cycles may also be used. The number of PMCA rounds required to produce a signal detectable by western blot was determined.

Figure 1:
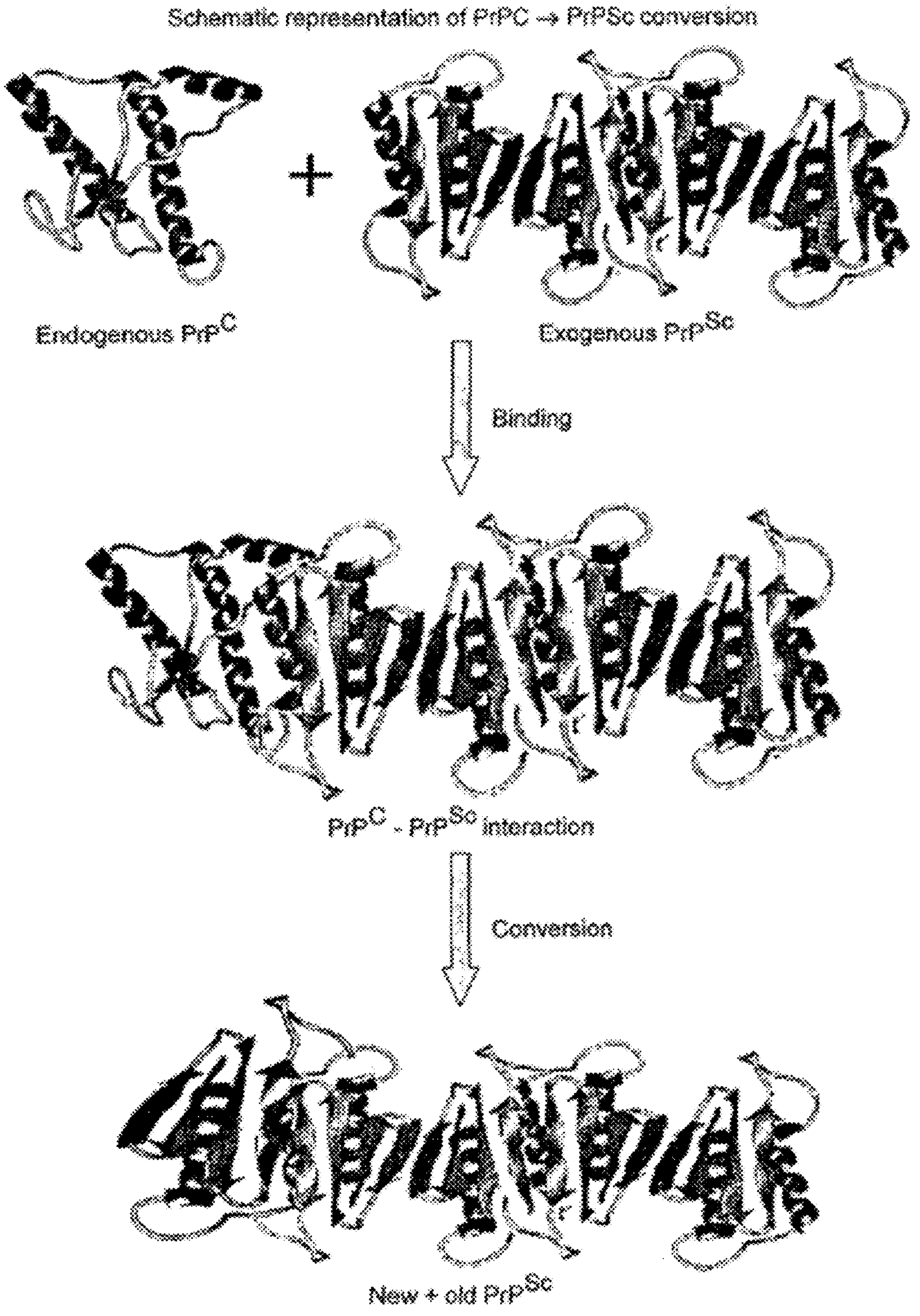
FIG. 1 illustrates an example schematic representation of the conversion of $PrP^C$ to $PrP^{Sc}$.
Figure 2:
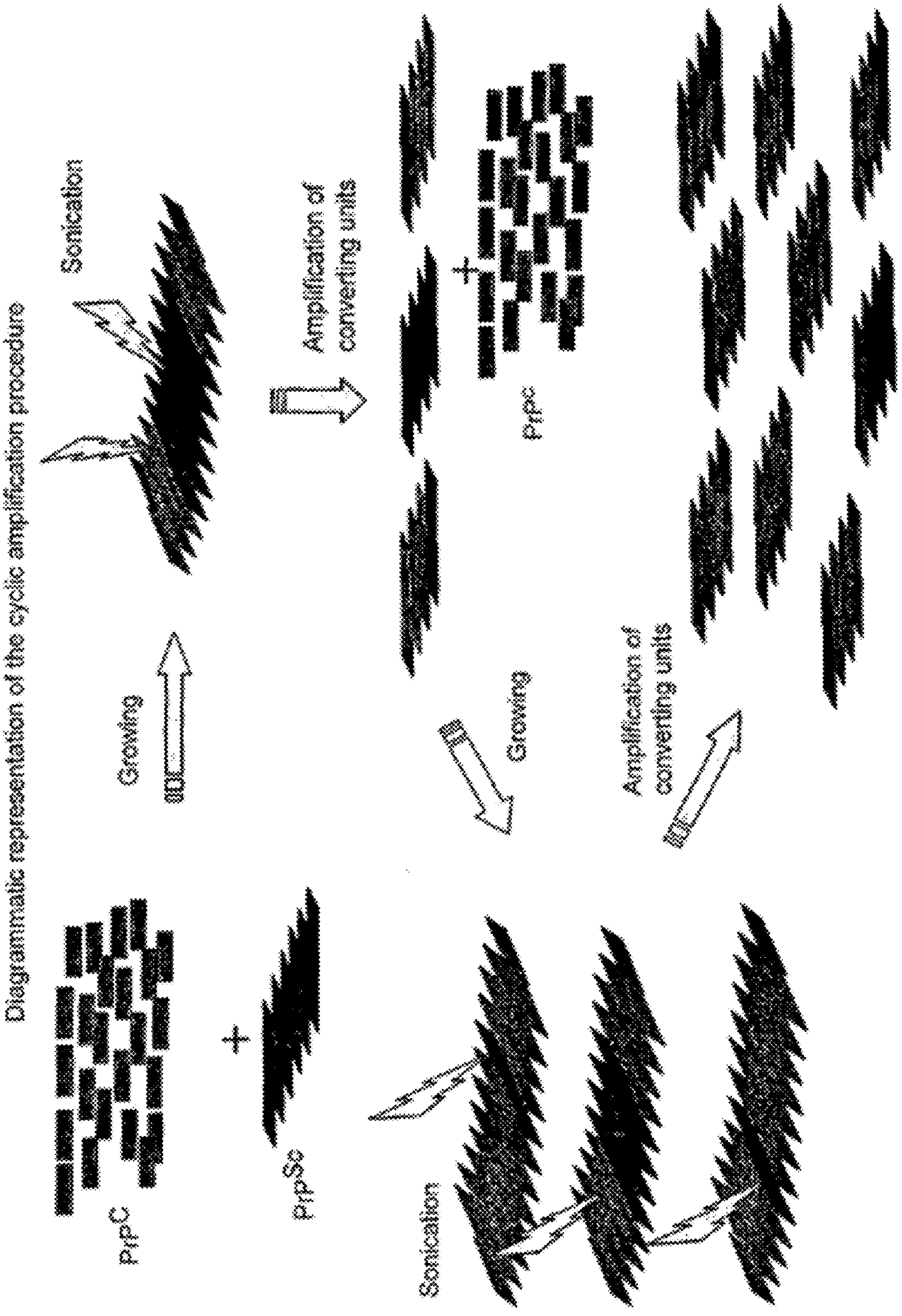
FIG. 2 illustrates an example diagrammatic representation of the protein misfolding amplification procedure.
Figure 3A:
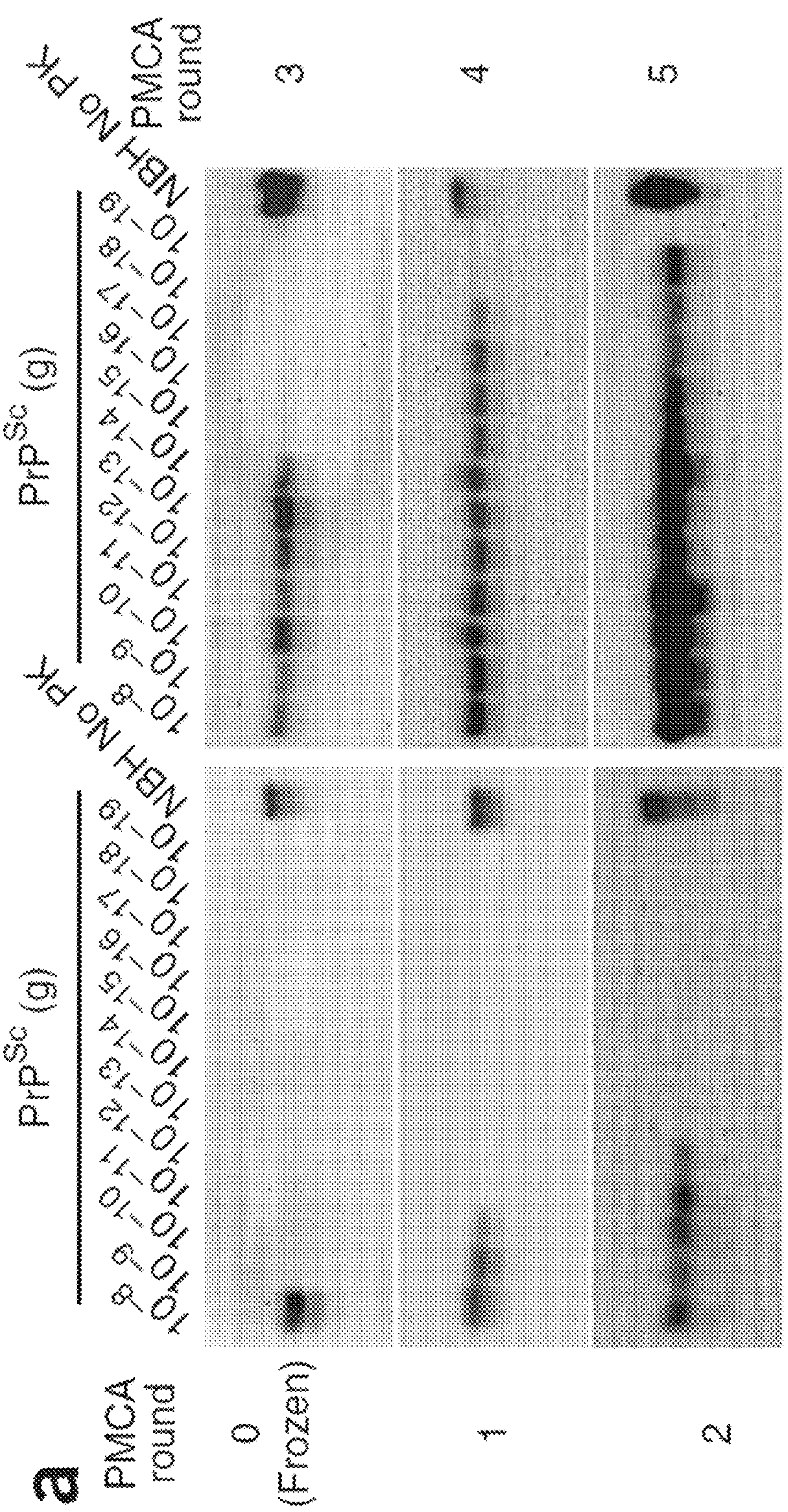
FIG. 3*a* illustrates western blot assays (3F4 antibody) of stock solutions of $PrP^{Sc}$ of various concentrations, upon being subjected to normal brain homogenate and serial rounds of PMCA (144 cycles).

FIG. 3*a* illustrates western blot assays (3F4 antibody) of the stock reaction mixes. All samples except the normal brain homogenate (NBH) used as a migration control were digested with proteinase K (PK).

Figure 3B:
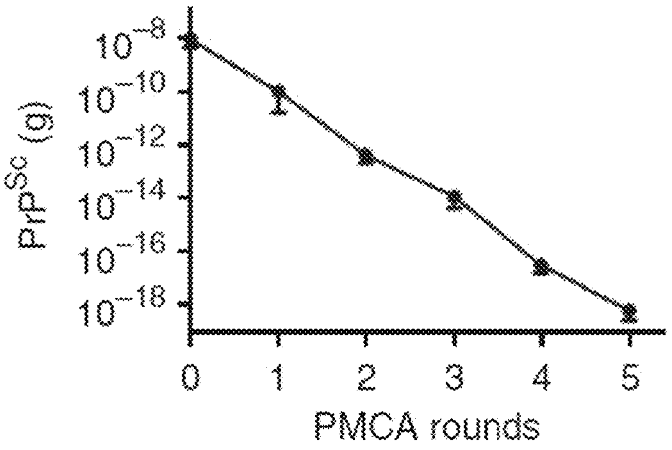
FIG. 3*b* illustrates a calibration curve, based on a plot of $PrP^{Sc}$ concentration vs. the number of PMCA rounds required to detect $PrP^{Sc}$ by western blot assay.

The concentrations of the sub-solutions were plotted against the number of PMCA rounds required for detection, to provide a calibration curve. The results are shown in FIG. 3*b*. More particularly, the western blots from FIG. 3*a* were analyzed by densitometry, and the last detectable signal after each PMCA round was plotted, yielding a standard calibration curve to estimate $PrP^{Sc}$ concentrations.

It was determined that there is a direct relationship between the quantity of $PrP^{Sc}$ in a given sample and the number of PMCA cycles necessary for its detection. By extrapolating the number of PMCA rounds required to detect an unknown sample, the concentration of $PrP^{Sc}$ in the sample may be estimated.

Thus, in one embodiment, an unknown sample may be subjected to a $PrP^{C}$ source to form a sample reaction mix. The sample reaction mix is incubated and subjected to sonication. The incubation and sonication steps may be repeated a plurality of times, until a $PrP^{Sc}$ signal is detected for the sample reaction mix. The number of times the incubation and sonication steps were repeated is compared to the predetermined calibration curve to determine the concentration of $PrP^{Sc}$ in the sample.

Figure 4:
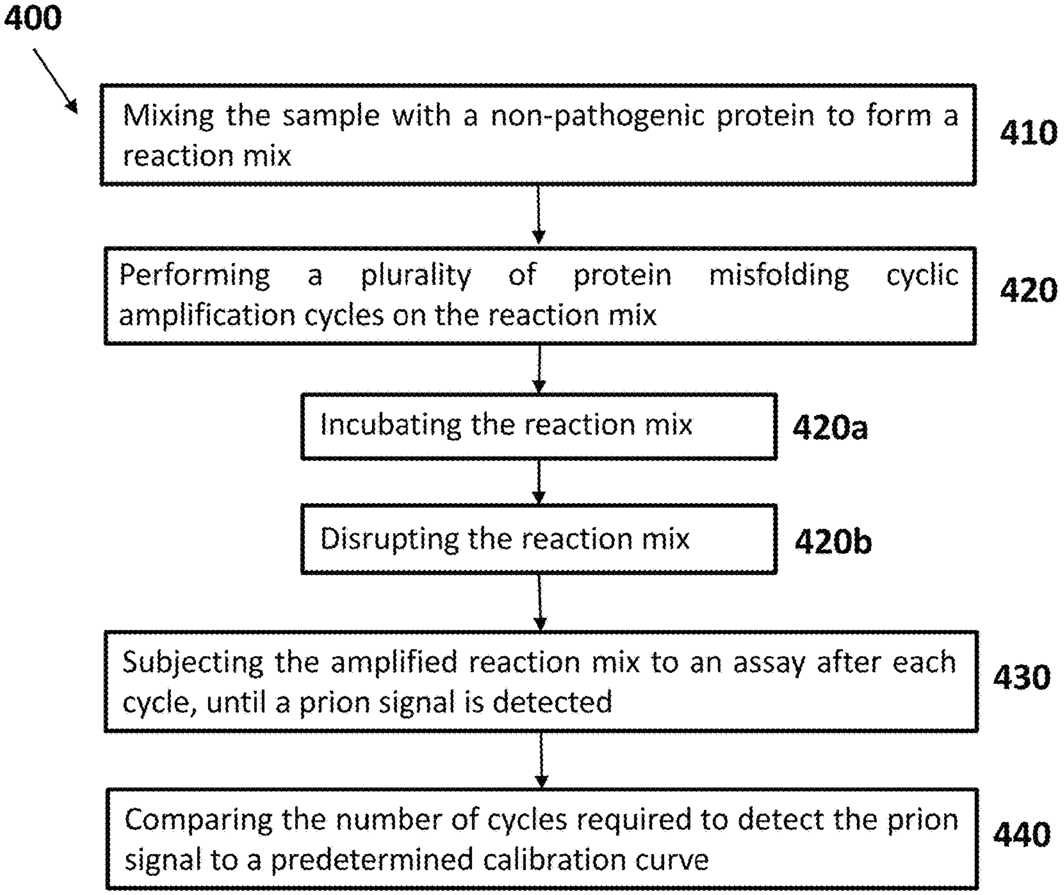
FIG. 4 is a flow chart of an example method for estimating the concentration of prion in a sample, where a predetermined calibration curve is provided.

In one embodiment, as depicted in FIG. 4, where a calibration curve is known and provided, e.g., as a part of a kit, a method 400 for estimating the concentration of prion in a sample may comprise:

mixing the sample with a non-pathogenic protein to form a reaction mix (step 410);

performing a plurality of protein misfolding cyclic amplification cycles on the reaction mix (step 420), each cycle comprising:

incubating the reaction mix (sub-step 420*a*); and disrupting the reaction mix (sub-step 420*b*);

subjecting the amplified reaction mix to an assay after each cycle, until a prion signal is detected (step 430); and comparing the number of cycles required to detect the prion signal to a predetermined calibration curve (step 440).

In one embodiment, a kit for detecting and quantifying prion in a sample is provided, the kit comprising:

(a) a non-pathogenic protein source;

(b) a sonicator; and (c) a calibration curve.

EXAMPLES

Example 1: Sample Preparation

Syrian hamsters were intraperitoneally inoculated with 263,000 prions and monitored for the appearance of clinical symptoms, using a standard scale known in the art. When disease was confirmed, urine was collected using metabolic cages. The hamsters were then killed by $CO_2$ inhalation, and brains, spleens, and blood were collected.

Brain and spleen homogenates were prepared at 10% (wt/vol) in PBS plus Complete cocktail of protease inhibitors (Boehringer Mannheim). The samples were clarified by a 45 s low speed centrifugation. Blood samples were obtained directly from the heart in tubes containing citrate. Plasma and buffy coat were separated by centrifugation in ficoll gradient. Samples of normal brain homogenate used for PMCA substrate were obtained after perfusing hamsters with PBS and 5 mM EDTA. Solutions of 10% normal brain homogenate were made in conversion buffer (PBS without $Ca^{2+}$ and $Mg^{2+}$ with 150 mM NaCl, 1.0% triton X-100, and Complete protease inhibitors). Debris was removed by a 45 s low speed centrifugation in an Eppendorf centrifuge.

Example 2: $PrP^{Sc}$ Partial Purification by Sarkosyl Precipitation

To minimize interference in PMCA from other components present in tissues and fluids, $PrP^{Sc}$ was partially enriched by sarkosyl precipitation. More particularly, samples were incubated with one volume of 20% sarkosyl for 10 min at room temperature and centrifuged at 100,000 g for 1 h at 4° C. Supernatants were discarded and pellets were re-suspended into two volumes of 10% sarkosyl. The centrifugation process was repeated, and pellets were re-suspended directly in 10% normal brain homogenate prepared in conversion buffer. Following this protocol, $PrP^{Sc}$ was recovered in the pellet fraction at greater than 90% yield.

Example 3: PMCA Procedure

Samples were loaded onto 0.2 mL PCR tubes. Tubes were positioned on an adaptor placed on a plate holder of a microsonicator (Misonix model 4000), and samples were subjected to cycles of 30 min incubation at 37° C., followed by a 20 s pulse of sonication set at a potency of 7.5 (75%). Samples were incubated, without shaking, immersed in the water of the sonicator bath. Standard PMCA rounds included 144 cycles. After each round of cycles, a 10 µL aliquot of the amplified material was diluted into 90 µL of normal brain homogenate and a new round of PMCA cycles was performed.

Example 4: $PrP^{Sc}$ Detection

Samples were digested with 50 µg $mL^{-1}$ of PK at 37° C. for 1 h, and the reaction was stopped by adding NuPAGE LDS sample buffer. The proteins were fractionated using 4-12% SDS-PAGE, electroblotted into Hybond ECL nitrocellulose membrane, and probed with the 3F4 antibody (Covance) (dilution 1:5,000). The immunoreactive bands were visualized by ECL Plus western blotting detection system and quantified by densitometry using a UVP Bioimaging System EC3 apparatus.

Example 5: Detection of $PrP^{Sc}$ in the Spleen of Scrapie-Affected Hamsters

As described in Example 1, samples of brain, spleen, blood, and urine were collected from five hamsters exhibiting clinical signs of disease after intraperitoneal inoculation with 263,000 prions. As described in Example 2, the $PrP^{Sc}$ was partially purified by sarkosyl precipitation to remove components that may affect PMCA efficiency. After centrifugation, $PrP^{Sc}$ pellets were re-suspended directly into healthy hamster brain homogenate and subjected to serial rounds of 144 PMCA cycles.

Figure 5:
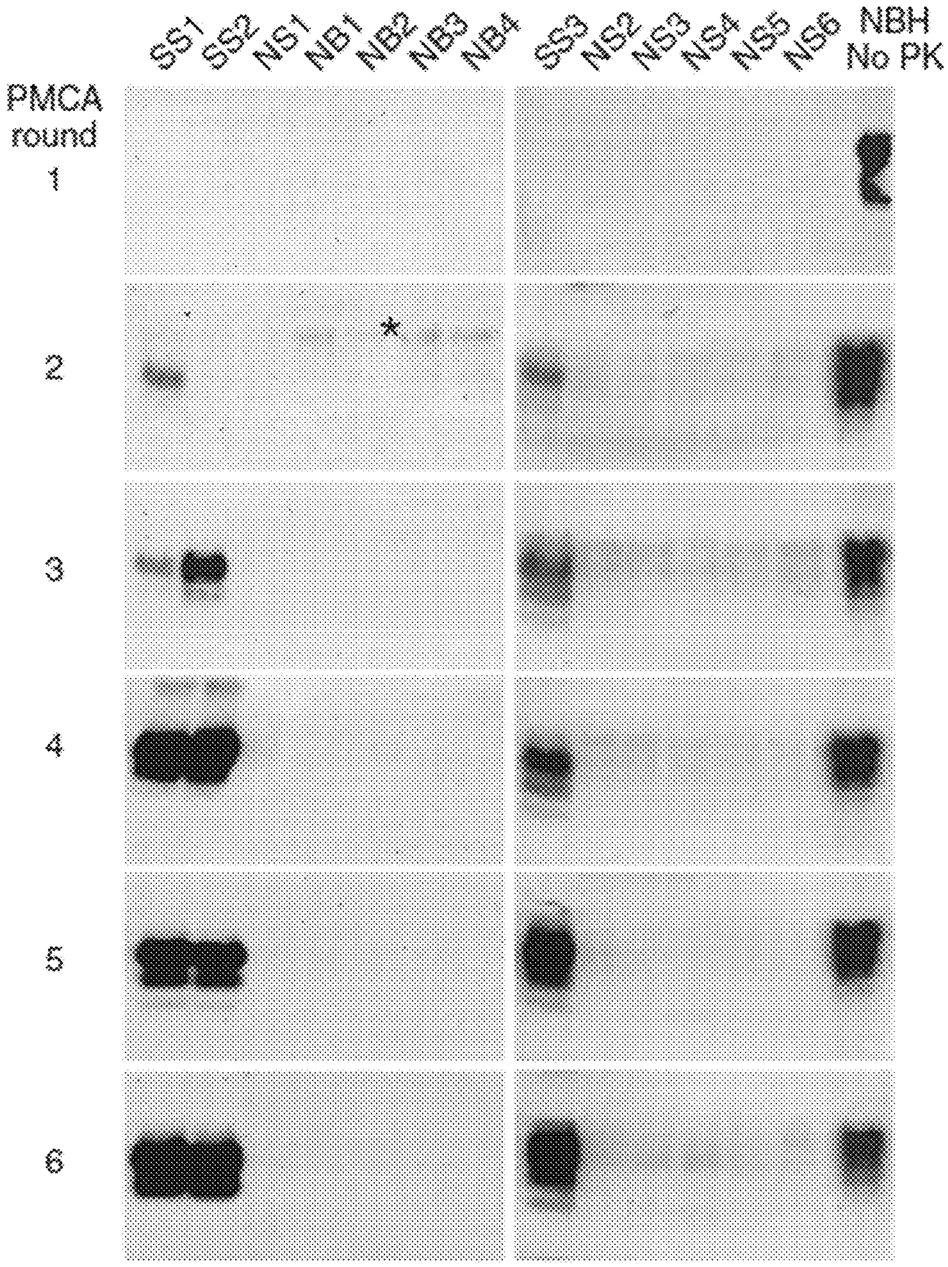
FIG. 5 illustrates western blot assays of $PrP^{Sc}$-affected hamster spleen suspended in normal hamster brain homogenate and subjected to serial PMCA, as compared to various control samples.

Three spleen samples were positive for prion disease. Of those three, $PrP^{Sc}$ was detectable after two rounds of PMCA for two samples and after the third round for the third sample. FIG. 5 illustrates western blot assays of $PrP^{Sc}$-affected hamster spleen suspended in normal hamster brain homogenate and subjected to serial PMCA. The three scrapie spleen samples are labeled SS1, SS2, and SS3.

With further reference to FIG. 5, control samples of normal (i.e., non-infected) spleen homogenate (samples NS1-NS6) and brain homogenate (samples NB1-NB4) were subjected to the same PMCA procedure to assess the rate of spontaneous appearance of $PrP^{Sc}$ reactivity. Normal brain homogenate (NBH) not digested with PK was used as a migration control. No $PrP^{Sc}$ signal was detected after six rounds of PMCA in any of the control samples.

Extrapolation from the calibration curve of FIG. 3*b* provides that the average concentration of $PrP^{Sc}$ in the symptomatic spleen was 20 pg $g^{-1}$. $PrP^{Sc}$ concentrations in other tissues and fluids were also analyzed. The results are shown in Table 1:

TABLE 1

$PrP^{Sc}$ Concentration in Scrapie-Affected Hampsters

| Source | $PrP^{Sc}$ Concentration in Tissues (g/g) and fluids (g/mL) |
|---|---|
| Brain | $2.3 \times 10^{-5} \pm 6.8 \times 10^{-6}$ |
| Spleen | $2.0 \times 10^{-11} \pm 1.1 \times 10^{-11}$ |
| Buffy Coat | $2.6 \times 10^{-13} \pm 2.4 \times 10^{-13}$ |
| Plasma | $1.3 \times 10^{-14} \pm 1.1 \times 10^{-14}$ |
| Urine | $2.0 \times 10^{-16} \pm 1.7 \times 10^{-16}$ |

Example 6: Dynamic Distribution and Quantification of $PrP^{Sc}$ in Different Tissues and Fluids To evaluate the application of quantitative PMCA to determine the concentration of prions in various tissues and fluids, and to understand the dynamic of $PrP^{Sc}$ formation and accumulation in tissues and fluids at distinct stages of the disease, $PrP^{Sc}$ levels in brains, spleens, blood fractions (plasma and buffy coat), and urine were measured at different time periods after infection.

Specifically, tissue extracts were obtained from hamsters intraperitoneally infected with 263,000 prions. Animals were sacrificed at the following time periods: 0, 2, 4, 9, 14, 21, 30, 43, 50, 71, 81, and 110 days post-inoculation. Under these conditions, animals showed the disease symptoms an average 110 days after inoculation. Samples from each of the tissues at each of the times from five different animals per group were suspended in normal hamster brain homogenate, subjected to serial rounds of PMCA, and subjected to western blotting.

Figure 6:
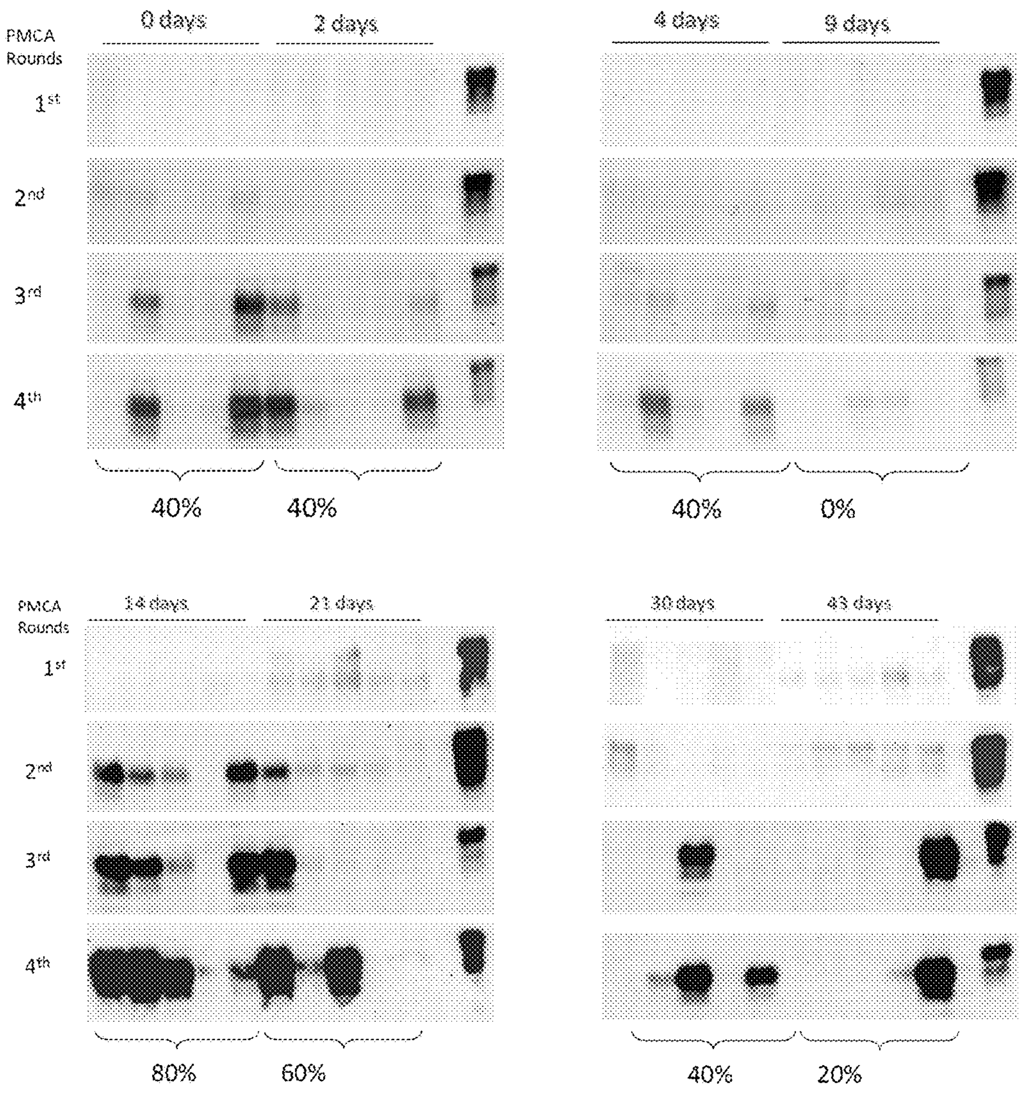
FIG. 6 illustrates western blot assays of $PrP^{Sc}$-affected hamster spleen suspended in normal hamster brain homogenate and subjected to serial PMCA. The samples were taken at various time periods after the hamsters were inoculated with $PrP^{Sc}$.

FIG. 6 illustrates western blot assays of the samples. The numbers at the top of the gels indicate the number of days after inoculation. The numbers to the left of the gels indicate the number of PMCA rounds. The numbers at the bottom of the gels indicate the percentage of $PrP^{Sc}$-positive animals after four rounds of PMCA.

Figure 7:
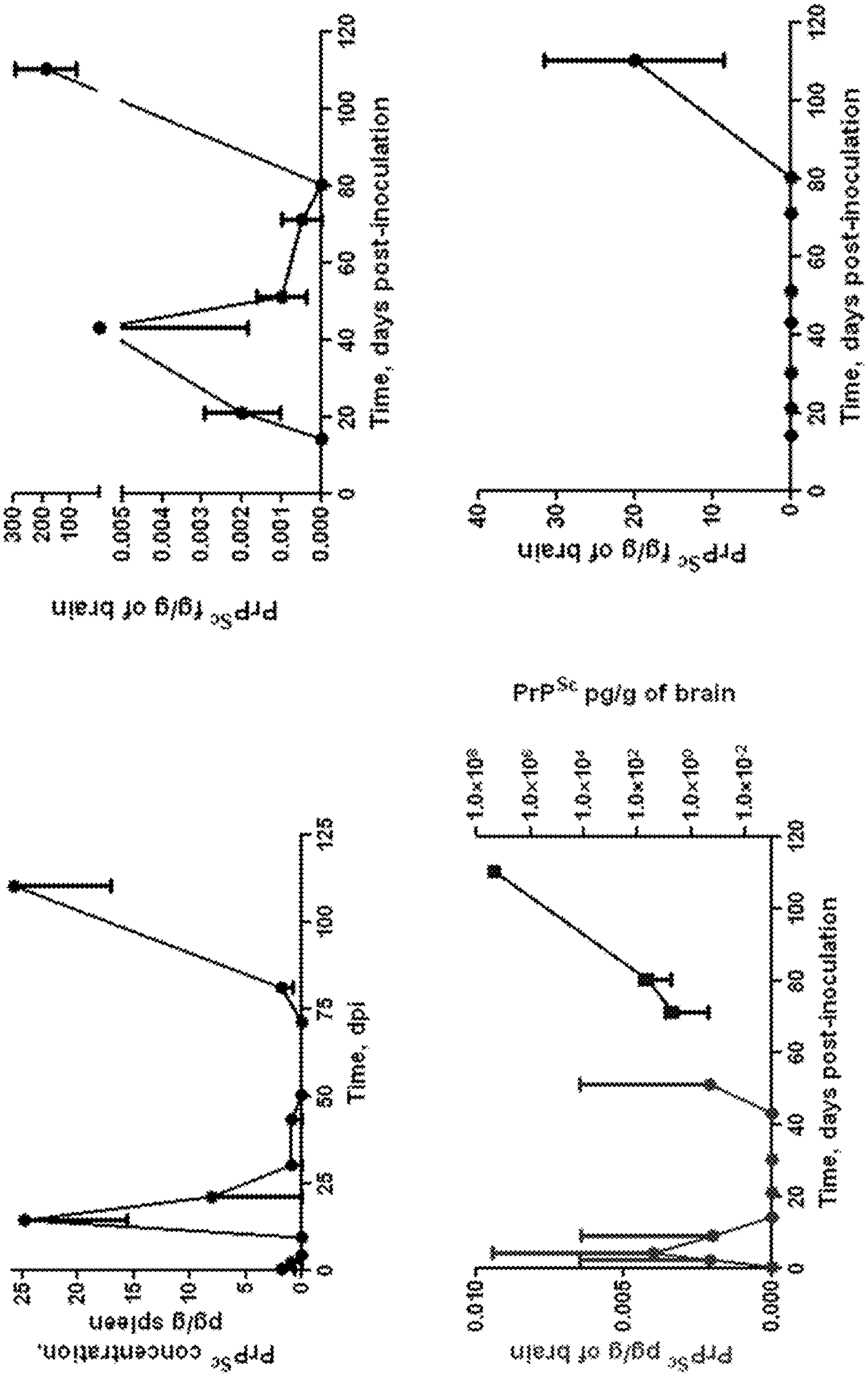
FIG. 7 illustrates plots of concentrations of $PrP^{Sc}$ in $PrP^{Sc}$-affected hamster spleen, brain, buffy coat, and plasma after serial rounds of PMCA. The samples were taken at various time periods after the hamsters were inoculated with $PrP^{Sc}$.

FIG. 7 illustrates plots of concentration versus the time period after inoculation for the various tissue and fluid samples. Endogenous replication of $PrP^{Sc}$ reached high levels in spleens at early stages after infection (FIG. 7, plot A), which correlated with their presence in white blood cells (FIG. 7, plot C). Interestingly, $PrP^{Sc}$ quantity decreased in spleens in the middle of the incubation periods, precisely prior to the time in which $PrP^{Sc}$ began to appear in the brain (FIG. 7, plot B). The levels of $PrP^{Sc}$ increased again in spleens close to the symptomatic phase, to reach a quantity similar to that found in the early pre-symptomatic stage of the disease (FIG. 7, plot A). The levels of $PrP^{Sc}$ in brains increased in an exponential way with time, starting around 50 days post-inoculation (FIG. 7, plot B). $PrP^{Sc}$ was not detectable in brains before this time, except for a few days after inoculation, which most likely represents the influx of $PrP^{Sc}$ present in the inoculum across the blood brain barrier. The quantities of $PrP^{Sc}$ estimated in brains two to nine days after inoculation reached around 2-4 fg/g of brain (FIG. 7, plot A). This quantity is probably not enough to trigger prion replication and is likely eliminated by the normal clearance mechanisms. The later re-appearance of $PrP^{Sc}$ in the brains likely means a more constant influx of prions produced by peripheral replication and transport through the peripheral nerves. The biphasic behavior of $PrP^{Sc}$ in spleens is similar to that expected in the blood buffy coat fraction, which mostly contains white cells. However, the quantities of $PrP^{Sc}$ in buffy coat are three orders of magnitude lower than those measured in spleens (FIG. 7, plot C). In plasma, $PrP^{Sc}$ was only detectable at or close to the symptomatic phase of the disease (FIG. 7, plot D), and the quantities are around 10 times lower than in the buffy coat fraction.

These findings indicate that the presence of $PrP^{Sc}$ in blood may have two different sources: peripheral replication in the spleen at early stages and brain leakage at late stages. Prions in blood at the pre-symptomatic phase are restricted to the white cells, which likely were coming from cells previously resident in the spleen. At the symptomatic phase, cerebral prions are likely leaking to the blood and circulate in a cell-free manner in plasma and possibly produce a second wave of spleen infection.

A comparison of the estimated quantities of $PrP^{Sc}$ in the organs and fluids tested at the symptomatic phase reveals that the quantity in the brain is 106, 108, and 109 times higher than in spleen, buffy coat, and plasma, respectively, in this particular model (Table 2). However, at half of the incubation period (50 days post inoculation) the quantity of prions in the brain is only around 2 fg/g, which represents only 3- and 2000-times higher than spleen and buffy coat (Table 2).

TABLE 2

Estimated $PrP^{Sc}$ Concentrations (g/g tissue or g/mL of fluid) in Different Tissues and Biological Fluids at Distinct Time Periods After Inoculation

| Source | Symptomatic (110 dpi) | Late Pre-Symptomatic (80 dpi) | Mid Pre-Symptomatic (51 dpi) | Early Pre-Symptomatic (21 dpi) |
|---|---|---|---|---|
| Brain | $2.3 \times 10^{-5} \pm 6.8 \times 10^{-6}$ | $5.1 \times 10^{-11} \pm 4.8 \times 10^{-11}$ | $2.2 \times 10^{-15} \pm 2.0 \times 10^{-15}$ | Not detectable |
| Spleen | $2.0 \times 10^{-11} \pm 1.1 \times 10^{-11}$ | $5.2 \times 10^{-13} \pm 6.8 \times 10^{-13}$ | $1.6 \times 10^{-16} \pm 1.2 \times 10^{-16}$ | $8.0 \times 10^{-12} \pm 7.1 \times 10^{-12}$ |
| Buffy Coat | $1.1 \times 10^{-13} \pm 0.9 \times 10^{-13}$ | Not detectable | $1.0 \times 10^{-18} \pm 1.0 \times 10^{-18}$ | $1.9 \times 10^{-18} \pm 1.2 \times 10^{-18}$ |
| Plasma | $5.2 \times 10^{-15} \pm 3.1 \times 10^{-15}$ | Not detectable | Not detectable | Not detectable |
| Urine | $2.0 \times 10^{-16} \pm 1.7 \times 10^{-16}$ | Not done | Not done | Not done |

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B), it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto."

While the present application has been illustrated by the description of particular embodiments, and while the embodiments have been described in considerable detail, it is not an intention to restrict or in any way limit the scope of the appended claims to such detail. With the benefit of the present application, additional advantages and modifications will readily appear to those skilled in the art. Therefore, the application, in its broader aspects, is not limited to the specific details and illustrative examples shown and described. Accordingly, departures may be made from such details without departing from the spirit or scope of the general inventive concept.

What is claimed is:

1. A method for preparing a calibration curve useful for quantitatively estimating a concentration of $PrP^{Sc}$ in a sample, the method comprising:

preparing a plurality of stock solutions, each stock solution in the plurality of stock solutions having a known different concentration of $PrP^{Sc}$;

separately mixing each of the plurality of stock solutions with $PrP^{C}$ to form a plurality of separate stock reaction mixes;

forming a plurality of separate amplified portions of $PrP^{Sc}$ by:

performing a plurality of protein misfolding cyclic amplification (PMCA) cycles on each of the plurality of separate stock reaction mixes to form a plurality of separate amplified stock reaction mixes comprising the plurality of separate amplified portions of $PrP^{Sc}$, each cycle in the plurality of PMCA cycles comprising:

incubating each stock reaction mix; and disaggregating aggregates formed in each stock reaction mix;

subjecting each of the plurality of separate amplified stock reaction mixes to an assay for a number of cycles of the plurality of PMCA cycles until a $PrP^{Sc}$ signal is detected; and determining the calibration curve according to the known different concentration of the $PrP^{Sc}$ in each stock solution with the number of PMCA cycles corresponding to detection of the $PrP^{Sc}$ signal, at least a portion of the known different concentrations of $PrP^{Sc}$ among the plurality of stock solutions being below a concentration detectable by the assay such that the calibration curve provides for quantitative estimation of $PrP^{Sc}$ concentration in the sample below the concentration detectable by the assay.

2. The method of claim 1, further comprising plotting the calibration curve in the form of a standard calibration curve.

3. The method of claim 1, wherein the $PrP^{C}$ is provided for mixing with each of the plurality of stock solutions in the form of a normal tissue homogenate.

4. The method of claim 1, wherein the assay is a western blot assay.

5. A method for quantitatively estimating a concentration of prion in a sample, the method comprising:

mixing the sample with a non-pathogenic $PrP^{C}$ protein to form a reaction mix;

forming an amplified portion of $PrP^{Sc}$ by:

performing a plurality of protein misfolding cyclic amplification (PMCA) cycles on the reaction mix to form an amplified reaction mix comprising the amplified portion of $PrP^{Sc}$, each cycle comprising:

incubating the reaction mix; and disaggregating aggregates formed in the reaction mix;

subjecting the amplified reaction mix to an assay for a number of the plurality of PMCA cycles until a $PrP^{Sc}$ prion signal is detected; and quantitatively estimating the concentration of the $PrP^{Sc}$ prion in the sample according to the number of PMCA cycles corresponding to detection of the $PrP^{Sc}$ prion signal by using a predetermined calibration curve for quantitatively estimating the concentration of the $PrP^{Sc}$ in the sample according to the assay, the predetermined calibration curve determined according to a plurality of known different concentrations of $PrP^{Sc}$ each corresponding to a calibrating number of PMCA cycles, each calibrating number of PMCA cycles being effective to amplify each corresponding known different concentration of $PrP^{Sc}$ in the presence of non-pathogenic $PrP^{C}$ to a concentration of $PrP^{Sc}$ detectable by the assay, at least a portion of the plurality of known different concentrations of $PrP^{Sc}$ being below the concentration detectable by the assay such that the predetermined calibration curve provides for quantitative estimation of $PrP^{Sc}$ concentration in the sample below the concentration detectable by the assay.

6. The method of claim 5, wherein the disaggregating comprises subjecting the reaction mix to sonication.

7. The method of claim 5, wherein the assay is a western blot assay.

8. The method of claim 5, further comprising:

removing a portion of the reaction mix;

contacting the portion with additional non-pathogenic $PrP^{C}$ protein to form a second reaction mix;

performing a plurality of PMCA cycles on the second reaction mix, each cycle in the plurality of PMCA cycles comprising:

incubating the second reaction mix; and disaggregating aggregates formed in the second reaction mix;

subjecting the disaggregated second reaction mix to an assay for a number of cycles of the plurality of PMCA cycles until the $PrP^{Sc}$ prion signal is detected; and quantitatively estimating the concentration of the $PrP^{Sc}$ prion in the second reaction mix according to the number of cycles corresponding to detection of the $PrP^{Sc}$ prion signal by using the predetermined calibration curve.

9. The method of claim 5, wherein the sample is selected from the group consisting of: spleen, brain, blood, and urine.

10. The method of claim 5, quantitatively estimating the concentration of the $PrP^{Sc}$ prion in the sample comprising quantitatively estimating the concentration of the $PrP^{Sc}$ below the concentration detectable by the assay.

* * * * *